(12) United States Patent
Ivanov et al.

(10) Patent No.: US 6,183,998 B1
(45) Date of Patent: Feb. 6, 2001

(54) METHOD FOR REVERSIBLE MODIFICATION OF THERMOSTABLE ENZYMES

(75) Inventors: Igor Ivanov, Martinsried/München; Dirk Löffert, Düsseldorf; Jie Kang, Erkrath; Joachim Ribbe, Düsseldorf; Kerstin Steinert, Langenfeld, all of (DE)

(73) Assignee: Qiagen GmbH Max-Volmer-Strasse 4, Hilden (DE)

( * ) Notice: Under 35 U.S.C. 154(b), the term of this patent shall be extended for 0 days.

(21) Appl. No.: 09/183,950

(22) Filed: Oct. 31, 1998

Related U.S. Application Data

(63) Continuation-in-part of application No. 09/086,846, filed on May 29, 1998, now abandoned.

(51) Int. Cl.[7] .............................. C12P 19/34; C12Q 1/68; C07K 1/00
(52) U.S. Cl. ............................. 435/91.2; 435/6; 530/350
(58) Field of Search ........................ 435/91.2, 6; 530/350

(56) References Cited

U.S. PATENT DOCUMENTS

| | | |
|---|---|---|
| 4,683,195 | 7/1987 | Mullis et al. . |
| 4,683,202 | 7/1987 | Mullis et al. . |
| 4,965,188 | 10/1990 | Mullis et al. . |
| 5,338,671 | 8/1994 | Scalice et al. . |
| 5,411,876 | 5/1995 | Bloch et al. . |
| 5,545,540 * | 8/1996 | Mian ................................. 435/91.2 |
| 5,677,152 | 10/1997 | Birch et al. . |
| 5,773,258 | 6/1998 | Birch et al. . |

FOREIGN PATENT DOCUMENTS 0 771 870 A1  5/1997 (EP) .............................. C12N/9/99

OTHER PUBLICATIONS

Kaledin et al., *Biokhimiia* (*USSR*), 46(9):1576–1584 (1981), with English abstract.
Means, *Methods In Enzymology*, 47: 469–478 (1977).
Schwartz et al., *Nucleic Acids Research*, 18(4): 1079 (1990).
Atassi et al., *Methods in Enzymology*, 25(B):546–553 (1972).
Amrute et al., *Biochemistry*, 33(27):8282–8291 (1994).
Butler et al., *Methods in Enzymology*, 25(B):191–199 (1972).
Chou et al., *Nucleic Acid Research*, 20(7):1717–1723 (1992).
Feldman et al., *Progr. Nucl. Acid Res. & Mol. Biol.*, 13:1–49 (1973).
Jackson et al., *Cell*, 15(3):945–954 (1978).
Kornberg et al., *DNA Replication*, Freeman & Co. (1980).
Means and Feeney, *Biochemistry.*, 7(6):2192–2201 (1993).
Saiki et al., *Science*, 230:1350–1354 (1985).
Sambrook et al., *Molecular Cloning—A laboratory Manual*, Cold Spring Harbor, N.Y. (1989).
Schwarz et al., *Nucleic Acid Research*, 18(4):10 (1990).
Uemori et al., *J. Biochem.* (*Japan*), 113(3):401–410 (1993).
Bell et al., *Proteins and Enzymes* (Prentice Hall, New Jersey) pp. 149–153 (1988).
Ulbrich , *Biomed. Biochim. Acta*, 47(9): 821 (1988), abstract only.
Zhao et al., *Jilin Daxue Ziran Kexue Xuebao*, 3:85–88 (1997), abstract only.
Shaffer A.L. et al, Amplification, detection, and automated sequencing of Gibbon Interleukin–2 mRNA by *Thermus aquaticus* DNA polymerase reverse transcription and polymerase chain reaction, Analytical Biochem., vol. 190, Nov. 1, 1990, pp 292–296.*

* cited by examiner

Primary Examiner—John S. Brusca
Assistant Examiner—Stephen Siu
(74) Attorney, Agent, or Firm—Leon R. Yankwich; David G. O'Brien

(57) ABSTRACT

A method for the amplification of a target nucleic acid is disclosed comprising the steps of reacting a nucleic acid with an amplification reaction mixture and a modified thermostable enzyme, wherein said modified thermostable polymerase is prepared by a reaction of a mixture of a thermostable polymerase and a chemical modifying reagent. The chemical modification reagent is an aldehyde, preferably formaldehyde. Essentially complete inactivation of the enzyme at ambient temperatures is achieved, with recovery of enzymatic activity at temperatures above 50° C.

40 Claims, No Drawings

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 1:

TTTCCCAGTC ACGACGTTGT AAAACGACGG      30

(2) INFORMATION FOR SEQ ID NO: 2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 2:

ACAAGGGAAG GCCAGGGAAT TTTC      24

(2) INFORMATION FOR SEQ ID NO: 3:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 3:

```
GGGCCATCCA TTCCTGGCTT TAAT                                              24

(2) INFORMATION FOR SEQ ID NO: 4:

(i) SEQUENCE CHARACTERISTICS:
        (A) LENGTH:24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

CTTCGCCCAC CCCGGGCTCG ATCC                                              24

(2) INFORMATION FOR SEQ ID NO: 5:

(i) SEQUENCE CHARACTERISTICS:
        (A) LENGTH:25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

CATGAAGCAC TTCACTGACA CCCTC                                             25

(2) INFORMATION FOR SEQ ID NO: 6:

(i) SEQUENCE CHARACTERISTICS:
        (A) LENGTH:20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

GCAACGCCCC TCACTATAAA                                                   20

(2) INFORMATION FOR SEQ ID NO: 7:

(i) SEQUENCE CHARACTERISTICS:
        (A) LENGTH:20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

GCACCCCGCC CTTGAAGTCC                                                   20

(2) INFORMATION FOR SEQ ID NO: 8:

(i) SEQUENCE CHARACTERISTICS:
        (A) LENGTH:24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

ATGGGGAAGG TGAAGGTCGG AGTC                                              24
```

```
(2) INFORMATION FOR SEQ ID NO: 9:

(i) SEQUENCE CHARACTERISTICS:
        (A) LENGTH:24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

AGTGTAGCCC AGGATGCCCT TGAG                                          24
```

METHOD FOR REVERSIBLE MODIFICATION OF THERMOSTABLE ENZYMES

CROSS-REFERENCE TO RELATED APPLICATIONS

This application is a continuation-in-part of U.S. application Ser. No. 09/086,846 filed May 29, 1998 now abandoned.

FEDERALLY SPONSORED RESEARCH

Research relating to the invention described below was supported under German BMBF Project Number 0311018.

FIELD OF THE INVENTION

The present invention provides a method for reversible inactivation of thermostable enzymes by chemical modification under aqueous conditions. This chemical modification of thermostable enzymes has surprising effects in applications in the field of molecular biology such as nucleic acid amplification.

BACKGROUND OF THE INVENTION

The most important nucleic acid amplification technology is the Polymerase Chain Reaction (PCR) which was first described by Saiki et al., *Science*, 230:1350–54 (1985) and is also disclosed in U.S. Pat. Nos. 4,683,202; 4,683,195; and 4,965,188. Commercial vendors, such as QIAGEN GmbH, Hilden, Germany, market PCR reagents and kits, and provide protocols for PCR.

The principle of PCR is basically described by the amplification of specific nucleic acid sequences of a nucleic acid target template, using at least one, two or several target-specific oligonucleotides (primers), a thermostable nucleic acid polymerase, deoxyribonucleoside triphosphates and a reaction buffer. DNA synthesis initiates at the accessible 3'—OH group of the target-specific oligonucleotides flanking the DNA sequence to be copied, thereby generating an identical copy of the target template nucleic acid sequence. The enzymatic reaction is repeated for a substantial number of thermal cycles consisting of the denaturation of the target nucleic acid, annealing of the primer oligonucleotides to complementary nucleic acid sequences and the subsequent extension of these primer-template complexes using a thermostable nucleic acid polymerase in a sequence-dependent manner. Hybridization of primers occurs usually at sufficiently high temperature to provide annealing conditions that ensure binding of the oligonucleotide primers mainly to its complementary target nucleic acid sequence. However, PCR reaction mixtures are often assembled at room temperature, thus providing much less stringent oligonucleotide hybridization conditions, at a temperature at which most thermostable nucleic acid polymerases possess DNA synthesis activity. Since non-specifically annealed and extended oligonucleotides lead to formation of non-specific amplification products, these mis-primed non-specific PCR products can compete during subsequent PCR cycles with the specific PCR product for primer molecules, polymerase and nucleotides, thereby severely interfering or even abrogating the amplification reaction of the specific amplification product (see, Chou et al., *Nucleic Acids Research*, 20(7): 1717–1723 (1992)).

To overcome difficulties related to non-specific amplification products caused by the extension of mis-primed oligonucleotides during the reaction set-up or the initial heating phase of PCR, an essential PCR component such as the oligonucleotide primers, nucleotide triphosphates, magnesium ions or thermostable nucleic acid polymerase could be added only at higher temperatures, thereby reducing the probability of having non-specific hybridization or extending mis-primed oligonucleotides. This technique is commonly known as "hot-start PCR", or more specifically "manual hot-start PCR".

Another method, described in U.S. Pat. No. 5,411,876, employs a solid wax-barrier between the template-primer mix and the remaining reaction mixture. This wax-barrier melts only at elevated temperature, so that all of the reaction components are mixed only at high temperature, preventing mis-priming and extension of mis-primed oligonucleotides. However, as in the case of the manual hot start PCR, the wax-mediated hot start procedure carries a higher risk of contamination and is less convenient, due to increased time necessary for sample processing and due to the solid wax-barrier that forms above the reaction mixture after finishing PCR.

Extension of mis-primed oligonucleotides can also be prevented by pre-incubating the primers with a compound that binds specifically to single-stranded DNA in a heat-reversible manner, such as a single-strand binding protein. Such a compound would prevent the oligonucleotide primer from hybridizing to any template sequence at ambient temperature. For instance, the use of Gene 32 protein, a single stranded DNA binding protein, was shown to improve the yield of PCR products in Schwarz et al., *Nucleic Acid Research*, 18(4): 10 (1990).

Another method of reducing formation of extension products from mis-primed oligonucleotides during the reaction set-up is a reversible non-covalent modification of the nucleic acid polymerase. U.S. Pat. No. 5,338,671 discloses the use of antibodies specific for the nucleic acid polymerase to inhibit the polymerase's activity. Pre-mixing of nucleic acid polymerase and polymerase-specific antibodies results in the formation of an antibody-polymerase complex. Under these conditions substantially no oligonucleotide extension activity can be detected. At elevated temperatures, the antibody dissociates from the complex, thus releasing the nucleic acid polymerase, which can then function in DNA synthesis during the Polymerase Chain Reaction. However, this method carries the risk of contamination due to an increased number of handling steps and the possible presence of residual nucleic acids derived from the antibody preparation. Another method to reduce non-specific amplification products involves the use of a chemically modified thermostable DNA polymerase that becomes active only after incubation of the DNA polymerase for a certain period of time at elevated temperature, thus preventing production of non-specific DNA synthesis products during reaction set-up and the initial heating phase of PCR. U.S. Pat. No. 5,677,152 and corresponding European patent publication EP 0 771 870 A1 describe a method for amplification of a target nucleic acid using a thermostable polymerase reversibly inactivated using a dicarboxylic acid anhydride.

Standard protocols of molecular biology applications, enzymology, protein and nucleic acid chemistry are well described in printed publications such as *Molecular Cloning*-A Laboratory Manual, Cold Spring Harbor, N.Y. (Sambrook et al. 1989); PCR Protocols-*A Guide to Methods and Applications*, Academic Press, N.Y. (Innis et al., eds, 1990), PCR Primer-*A Laboratory Manual*, CSHL Press (Dieffenbach and Dveksler, eds., 1995); and *Methods in Enzymology*, Academic Press, Inc. All of the patents, patent applications, and publications cited herein are incorporated by reference.

SUMMARY OF THE INVENTION

The present invention provides methods and reagents for reversible inactivation of thermostable enzymes using a chemical modification under essentially aqueous conditions. In particular, the thermostable enzymes of the present invention are reversibly modified in the presence of an aldehyde. The modified thermostable enzymes of the present invention do not show significant increase in enzyme activity at 37° C., even when incubated for periods of an hour or more. On the other hand, enzymatic activity of the present chemically modified enzymes is increased at least two-fold within thirty minutes when incubated at a more elevated temperature, i.e., above 50° C., preferably at a temperature of 75° C. to 100° C., and most preferably at 95° C. Such chemically modified enzymes may be employed in all applications involving manipulation of nucleic acids, such as amplification, ligation, exonucleolytic or endonucleolytic reactions, or nucleic acid topology changing enzymatic reactions, wherein the inactivated enzyme becomes reactivated by incubating the reaction mixture prior or as part of the intended enzymatic reaction at an elevated temperature.

One major aspect of the modification is crosslinking of enzyme molecules, thereby limiting enzyme structure flexibility and accessibility of functional core region(s) of the enzyme. The great advantage of this method is its broad applicability, since the inactivation and reactivation of the thermostable enzyme is essentially independent of pH, which in general varies with respect to the optimal reaction conditions for different enzymes.

Another aspect of the present invention relates to methods for chemical modification of thermostable enzymes such as enzymes for nucleic acid amplification reactions, ligation reactions or enzymatic reactions requiring exo- and/or endonucleolytic activities or enzymatic reactions resulting in changes of nucleic acid topology.

A further aspect of the present invention relates to the chemical modifier employed for reversible inactivation of the thermostable enzymes of the present invention. Preferably the chemical modifier is capable of reversibly modifying the enzymes of the present invention under essentially aqueous conditions. More preferably, the chemical modifier is an aldehyde. Most preferably the chemical modifier is formaldehyde ($H_2C=O$).

Formaldehyde, particularly, is a preferred reagent for reversible inactivation of thermostable DNA polymerases from the genera Thermus, Pyrococcus Thermococcus and Thermotoga, preferably *Thermus aquaticus, Pyrococcus furiosus, Pyrococcus woesei,* Pyrococcus spec. (strain KOD1), Pyrococcus spec. GB-D, Thermococcus Litoralis Thermococcus sp. 9° N-7, *Thermotoga maritima,* Pyrococcus spec. ES4 (*endeavori*), Pyrococcus spec. OT3 (*horikoshii*),*Pyrococcus profundus, Thermococcus stetteri,* Thermococcus spec. AN1 (*zilligii*), *Thermococcus peptonophilus, Thermococus celer* and *Thermococcus fumicolans,* for use in primer extension reactions. The preferred method of modification consists in crosslinking molecules of thermostable enzyme, e.g. Taq DNA polymerase, by reaction with formaldehyde. The crosslinked Taq DNA polymerase treated with formaldehyde has essentially no primer extension activity at the conditions of maximal primer extension activity (between 60° C. to 75° C.), as is shown in Example 6; and it appears to be more stabilized in comparison with Taq DNA polymerase treated with anhydride. Modification of the Taq DNA polymerase enzyme structure as described herein may prevent the enzymatic activity by reducing, for example, flexibility of the structure or reducing accessibility of the active core region of the enzyme by crosslinking enzyme molecules. Binding to the template, adding the deoxyribonucleoside triphosphates and moving along the template may require specific enzyme conformations and flexibility as well as free accessibility of the enzyme's active center.

In another aspect, the present invention relates to PCR additives which affect the melting behavior of nucleic acids, to be used in combination with aldehyde-inactivated DNA polymerase, particularly formaldehyde-inactivated Taq DNA polymerase, to improve PCR reactions. Such PCR additives are useful in the PCR reactions for amplification of difficult DNA template sequences such as, for example, templates with a high GC content or extensive secondary structure. A particularly preferred additive for this purpose is betaine

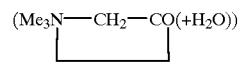

and other zwitterionic bases characterized by the $^-OOC-CH_2-NMe_3^+$ group (collectively "betaines"). Additional PCR additives include multifunctional polyols, preferably trifunctional polyols, most preferably glycerol; amides, preferably carbamides, most preferably formamide; alkaline ammonia salts, preferably alkylated ammonia salts, most preferably tetramethylammonium chloride; sulfoxides, preferably alkylated sulfoxides, most preferably dimethylsulfoxide; sulfates, preferably inorganic sulfates, most preferably ammonium sulfate polyalkylene glycols, most preferably polyethylene glycol. Additionally, SSB protein (single strand binding protein), preferably *E. coli* SSB protein, T4 gene 32 protein, yeast SSB protein, may also be used. Preferred PCR additives also include calf thymus protein UP1.

In another aspect, the present invention relates to the use of RNase H positive and RNase H negative reverse transcriptases in combination with inactivated Taq DNA polymerase for a continuous reverse transcription polymerase chain reaction (RT-PCR) to be performed in a single reaction tube without interrupting the enzymatic reactions by additional handling steps.

Another aspect of the present invention relates to kits comprising such an inactivated thermostable enzyme together with a Tris-buffered reaction buffer or Tris-buffered reaction mixture.

These and other aspects and advantages of the invention will be apparent from the description and examples presented below.

DETAILED DESCRIPTION OF THE INVENTION

Modification Under Aqueous Conditions

The present invention relates to methods for chemical modification of thermostable enzymes such as enzymes for nucleic acid amplification reactions, ligation reactions, enzymatic reactions requiring exo- and/or endonucleotlytic activities or enzymatic reactions which result in changes of nucleic acid topology. The modified thermostable DNA polymerases according to the present invention exhibit stable, reduced enzyme activity at temperatures lower than about 50° C., and thus the presently disclosed reversibly inactivated enzymes show advantages over, e.g., a DNA polymerase treated as described in European patent publication EP 0 771 870 A1, as demonstrated in Examples 9, 12 and 13 below, due to the conditions necessary for reactivation and more specifically due to the discrepancy between the pH range required for reactivation and the pH that is allowed for optimal reaction conditions for such treated thermostable enzymes. Furthermore, modification of enzymes with acylating agents as described in EP 0 771 870 A1 is disadvantageous compared with the method described herein: Reactions employing acylating agents usually require non-aqueous reaction conditions, which are less suitable for proteins in terms of optimization and control of the modification reaction. In contrast, modification reactions using aldehydes, preferably formaldehyde, are advantageously carried out under essentially aqueous conditions and are therefore can be completed rapidly and are easy to optimize.

The present invention describes a method and reagents that can be used for the heat-reversible inactivation of thermostable enzymes that can be employed in primer-based nucleic acid amplification reactions. The present methods and reagents are especially suitable for nucleic acid polymerases that do not function satisfactorily when treated as described in European patent publication EP 0 771 870 A1, as is demonstrated in example 12.

The present invention provides methods for the convenient inactivation of enzymes that are thermostable, that is, enzymes that are relatively stable to heat and can withstand high temperature incubation (e.g., greater than about 50° C.) without irreversible loss of activity. Activity of the modified enzymes according to the invention can be achieved by treating said inactivated enzymes at high temperature (e.g., greater than about 50° C.) in a pre-incubation step prior to the intended enzymatic reaction or as part of the enzymatic reaction.

Aldehydes useful as modifying reagents for reversibly inactivating thermostable enzymes according to this invention will have the general formula RHC=O, where R is H or an alkyl, aryl, or alkylaldehyde (O=CH—(CH$_2$)$_{0-9}$—) group of 1 to 10 carbon atoms. Such reagents include formaldehyde, acetaldehyde, glutaraldehyde, and the like, however, because the aldehyde is believed to inactivate the enzyme by forming crosslinks between enzyme molecules, formaldehyde is especially preferred. The aldehyde employed must be at least partially soluble in water and capable of reacting below about 50° C. with the thermostable enzyme to form a modified enzyme that will return at least part of its former enzymatic primer extension activity after incubation at a high temperature, i.e., above about 50° C. It is believed that reaction of the enzyme with aldehyde reagent forms heat-labile crosslinks through aminofunctional side-chains, and therefore any aldehyde compound that is reactive with an enzyme to be treated and which forms such crosslinks without significantly degrading the enzyme or irreversibly inactivating the enzyme is suitable. The preferred reagent for the reversible inactivation of thermostable DNA polymerases for the use in primer extension reactions is formaldehyde.

The modification consists of reacting molecules of a thermostable enzyme, e.g., Taq DNA polymerase, by heating in the presence of 0.01 M–2 M aldehyde, e.g., formaldehyde, at a temperature below 50° C. (preferably 35° C.–39° C., most preferably about 37° C.), preferably under aqueous conditions, for sufficient time to reduce the activity of the enzyme to acceptable levels. The modification typically can be carried out within 1 to 60 minutes reaction time, but this will vary slightly depending on the reagent used. Formaldehyde modification will preferably be carried out for less than 60 minutes, most preferably 15 to 30 minutes. The modified thermostable enzyme will have essentially no primer extension activity at room temperature and will not recover significant activity until exposed to elevated temperatures. Below about 50° C., however, exposure must be so prolonged (greater than 1 hour) in order to reactivate the enzymes that the enzyme modification is viewed as being reversible only at high temperatures (above 50° C.). In a preferred embodiment, for example, a modified Taq DNA polymerase treated with formaldehyde according to the present invention has essentially no primer extension activity at the conditions of maximal primer extension activity (i.e., between 60° C. to 75° C.), as shown in Example 6; and the modified thermostable enzyme appears to be further stabilized in comparison with Taq DNA polymerase treated with anhydride.

Primer extension using a nucleic acid polymerase can be considered as a process involving two major stages. The first step is the association of the nucleic acid polymerase with a priming site. The second is binding of a nucleotide (to form a new base pair with the template nucleotide) and moving on to the next (unpaired) template nucleotide. At this point, the enzyme can dissociate or continue adding new deoxymononucleotides (Kornberg, *DNA replication*, Freeman & Co., New York, 1980). Modification of the enzyme structure by crosslinking with aldehyde reagents according to this invention is believed to prevent the enzymatic activity by reducing, for example, flexibility of the structure or reducing accessibility of the active core region of the enzyme by crosslinking enzyme molecules. Binding to the template, adding the deoxyribonucleoside triphosphates and moving along the template may require specific enzyme conformations and flexibility as well as free accessibility of the enzyme's active center that are hindered when the enzyme is in the crosslinked state.

Modification of proteins with formaldehyde that eliminates enzymatic activity has been shown in the art, however recovery of enzymatic activity of the formaldehyde-modified enzyme has not been observed. Earlier studies have shown that treatment of ribonuclease A by formaldehyde shows an immediate loss of enzymatic activity upon adding formaldehyde, followed by a slower second stage loss. The initial inactivation was reversed upon dilution and short incubation whereas the second stage of inactivation was not reversed by dilution (Means and Feeney 1968, *Biochemistry* 7(6): 2192–201). Surprisingly, we have found that the enzymatic activity of formaldehyde-treated thermostable enzymes can be recovered by incubation for a period at elevated temperatures.

Crosslinking of the enzyme can have additional stabilizing effects. Various physical studies have shown that the action of formaldehyde on proteins under conditions close to physiological conditions may produce intramolecular crosslinks hindering denaturation of proteins. Reductive alkylation with formaldehyde has little or no effect on the distribution of charged groups and causes a minimal disturbance of electrostatic interactions (see, Means, *Methods in Enzymology*, 47: 469–78 (1977)). Formaldehyde treatment, e.g., to fix or inactivate enzyme activity, has been used for a number of purposes. Formaldehyde has been used more extensively than other aldehydes in industry, research and medicine, e.g., for preparation of vaccines, inactivation of viral RNA, for making direct functional changes of nucleic acids in vivo, and for the investigation through modification of structural and functional characteristics of DNA and proteins (Feldman, *Progr. Nucl. Acid Res. & Mol. Biol.*, 13: 1–49 (1973)).

As described in EP 0 771 870 A1, reaction of most acylating agents, e.g., citraconic anhydride, with protein amino-groups is competitive with hydrolysis of the reagent by water or hydroxyl ions. The reaction conditions must be adjusted to take this into account, and non-aqueous solutions may be required for optimal performance. The optimal conditions employ a high concentration of the anhydride reagent at a pH that maximizes deprotonation of amino-groups but minimizes hydrolysis. The rapid liberation of acid during the reaction must also be taken into account, especially during the long incubation times, which are typical for the reaction (Atassi et al., *Methods in Enzymology,* 25(B): 546–53 (1972); Butler et al., *Methods in Enzymology.* 25(B): 191–199 (1972)).

In contrast to anhydride reagents, the reaction conditions of formaldehyde treatment are preferably aqueous. The reaction can be carried out at a broad range of pH in a few minutes. This fact simplifies optimization and control of the reaction rate.

As mentioned above, the primary sites of formaldehyde treatment appear to be the $\epsilon$—$NH_2$ group of lysine, e.g., in the histones. This group has a pK of 11.3 and at pH 7 is fully protonated and highly reactive. The rate of formaldehyde crosslinking of histones with DNA is very rapid (80% crosslinked within 1 min.). The dramatic decrease of ribonuclease activity is achieved after a few minutes upon addition of formaldehyde (Jackson, *Cell,* 15(3): 945–54 (1978)). The reaction of formaldehyde with an amine is thought to be an essential step. At the same time there is no consensus on the exact mechanism of formaldehyde action on the amino-groups of a protein. No evidence for so-called Schiff base (R—N=CHR) formation was obtained in the reaction of formaldehyde with $\alpha$-amino groups of amino acids although reductive alkylation of amino groups in protein by formaldehyde in the presence of pyridine borane and borohydride propose the mechanism of Schiff-formation.

Treatment of Thermostable Enzymes

In a preferred method, DNA polymerase purified from *Thermus aquaticus* is incubated with up to 2 M formaldehyde, preferably with 20 mM to 1 M formaldehyde, at 37° C. in a water bath, for about 1 minute to 60 minutes, preferably 30 minutes. Subsequently, the reaction mixture is chilled on ice and the residual formaldehyde is removed from the formaldehyde-treated DNA polymerase by ultrafiltration and by washing in a buffer consisting of 20 mM Hepes pH 7.9, 1 mM EDTA, 200 mM KCl. The treated DNA polymerase is then dialyzed overnight at 4° C. against a storage buffer consisting of 20 mM Tris pH 9.0, 0.1 mM EDTA, 0.5% (v/v) Tween 20, 10 mM ethanolamine, 100 mM KCl, 1 mM DTT, 0.5% (v/v) Nonidet P-40, 50% (v/v) Glycerin. Surprisingly, it was found that formaldehyde treatment of thermostable nucleic acid polymerase isolated from either *Thermus aquaticus* or *Pyrococcus furiosus,* cloned and overexpressed in *Escherichia coli,* under essentially physiological conditions gives a stable product after removal of unreacted formaldehyde.

The formaldehyde-modified nucleic acid polymerases are characterized by non-detectable primer extension activity, in the absence of free formaldehyde. In addition, the primer extension activity can be recovered by incubation at elevated temperature for a prolonged time. The recovery of primer extension activity was found to be temperature-dependent and time-dependent, with higher reactivation temperature or longer incubation times above 50° C. leading to greater or more rapid recovery of activity. Furthermore, reactivation of formaldehyde-treated nucleic acid polymerase is essentially independent of pH. Most reaction buffers or reaction mixtures are Tris-buffered. The temperature dependence of many buffer systems used in molecular biology including Tris-buffers has been reported by Good et al., *Biochemistry,* 5(2): 467–477 (1966). With regard to Tris-buffers, the change in pKa with temperature is as follows: $\Delta pKa/°C.=-0.031$. As indicated in the following examples, it is shown that recovery of enzyme activity from formaldehyde-treated thermostable DNA polymerase is more temperature-dependent and less pH dependent than, for example, when using dicarboxylic acid anhydrides.

In addition to using the modified, inactivated nucleic acid polymerases as described above, PCR reactions may be improved by using additives that affect the melting behavior of nucleic acids in the reaction mixture. For example, difficult PCR amplifications, such as reactions that yield non-specific products, and especially amplification of templates having a high GC content or having extensive secondary structure, may be improved by employing additives that "isostabilize" AT- and GC-base pairing to the level of AT-base pair stability. Suitable such PCR additives include multifunctional polyols, preferably trifunctional polyols, most preferably glycerol; amides, preferably carbamides, most preferably formamide; alkaline ammonia salts, preferably alkylated ammonia salts, most preferably tetramethylammonium chloride; sulfoxides, preferably alkylated sulfoxides, most preferably dimethylsulfoxide; sulfates, preferably inorganic sulfates, most preferably ammonium sulfate polyalkylene glycols, most preferably polyethylene glycol. Additionally, SSB protein (single strand binding protein), preferably *E. coli* SSB protein (see, Schwarz et al., *E. coli* SSB protein, *Nucleic Acids Research,* 18: 1079 (1990)), T4 gene 32 protein, or yeast SSB protein, may also be used. Preferred PCR additives also include calf thymus protein UP1 (see, Amrute et al., *Biochemistry,* 33(27): 8282–8291 (1994).

A particularly preferred PCR additive for this purpose is betaine (1-carboxy-N,N,N-trimethyl-methanaminium inner salt) and other zwitterionic bases characterized by the $^-OOC$—$CH_2$—$NMe_3^+$ group (collectively "betaines").

The PCR additives are advantageously added to a PCR reaction mixture in an amount effective to improve the specificity of the amplified product. Typically concentrations of additive from 1 mM to 5M, preferably about 1M, are used, however any amount that improves the yield of the specific amplification product, compared with a PCR reaction carried out in the absence of the additive, is suitable.

In PCR reactions involving reverse transcription (RT-PCR), the materials and methods of the present invention permit a continuous reaction to be carried out in one vessel, without interrupting the enzymatic reactions by additional handling steps.

Preferred embodiments of the present invention are demonstrated in the Examples to follow. The Examples are provided as illustrations, and not as a limitation, of the scope of the present invention.

EXAMPLES

Example 1

Activity Measurement of Thermostable DNA Polymerases Using a Primer Extension Reaction This example shows an assay for measuring the primer extension activity of thermostable DNA polymerases. The assay is based on the difference in mobility of single- and double-stranded DNA molecules on an agarose gel in the presence of a DNA-intercalating dye. Annealing of a primer to a single-stranded DNA molecule creates a priming site for the DNA polymerase. Depending on reaction time and amount of polymerase, the primer can be extended to convert the single-stranded DNA into double-stranded molecules.

A reaction mixture of 50 ng M13mp18 DNA (20 fmol; 7250 nt), 0.1 µM 30-mer oligonucleotide primer 5'-TTTCCCAGTCACGACGTTGTAAAACGACGG-3' (SEQ ID NO: 1), 50 µM of each dNTP in 10 µl of 10 mM Tris HCl pH 8.8, 50 mM KCl, 1.5 mM MgCl$_2$ (Taq DNA polymerase) or 10 µl of 20 mM Tris.Cl pH 8.8; 10 mM KCl; 10 mM (NH$_4$)$_2$SO$_4$; 2 mM MgSO$_4$; 0.1% Triton X-114 (Pfu DNA polymerase) was prepared and divided into polypropylene reaction tubes. Each tube received a different amount of DNA polymerase (0.25, 0.15., 0.05, 0.03, 0.01 units). The DNA polymerase was diluted in 10 mM Tris-HCl pH 8.8, 50 mM KCl buffer containing 1 µg/ml BSA to compensate for possible protein interactions with the surface of the polypropylene reaction tube.

Primer extension reactions were performed in a Biometra UnoII Thermocycler (Biometra, Göttingen, Germany) using the following reaction profile: 94° C. for 1 sec., 55° C. for 30 sec., 72° C. for 3 min. Heating of the reaction mixture to 94° C. was done to destroy possible secondary structures of the single-stranded M13 DNA and to facilitate specific primer annealing during the lowering of reaction temperature to 55° C. Results of primer extension reactions at 72° C. were reproducible. After completing the reaction, each sample was mixed with 1 µl gel loading solution (50% Glycerol, 1xTAE buffer, 0.02 mg/ml Bromphenol blue) and loaded on a 1% agarose gel containing 0.5 µg/ml ethidium bromide. The gel was run at 80 mA for 15 min. in 1xTAE buffer. These conditions facilitated discrimination between extended- (ds) and non-extended (ss) M13 DNA fragments.

For reactivation experiments of inactivated enzymes, the assay was performed as described above, except incubation was performed with a primary reactivation step at 95° C. for indicated time periods.

Example 2
Unit Assay for Determination of DNA Polymerase Activity

This example shows the unit determination of DNA polymerase activity. One unit Taq DNA polymerase is defined as the amount of enzyme that will incorporate 10 nmoles of dNTPs into acid insoluble material within 30 min. at 72° C.

12.5 µg of sonicated herring sperm DNA were incubated with 0.01–0.1 unit of polymerase in assay buffer (25 mM TAPS pH 9.3 at 20° C.; 50 mM KCl; 2 mM MgCl$_2$; 1 mM DTT; 200 µM each dNTP; 100 µCi [α-$^{32}$P]dCTP) at 72° C. for 30 min. The amount of incorporated dNTPs is determined by trichloracetic acid precipitation. Units of inactivated enzymes were measured with a pre-incubation step of 3 hours at 80° C. resulting in complete recovery of enzyme activity.

Example 3
Preparation of Inactivated Taq DNA Polymerase Using Formaldehyde

This example describes the modification of Taq DNA polymerase with formaldehyde. Taq DNA polymerase was modified in a buffer containing 200 mM KCl; 1 mM EDTA; 20 mM HEPES; pH 7.9 at enzyme concentrations of 10–20 U/µl. Formaldehyde was purchased from Merck as a 37% stock solution. Immediately before use, 100 µl of formaldehyde were diluted with 168 µl of distilled water to yield a formaldehyde stock solution. Different amounts (40 µl to 800 µl) of this stock solution were mixed with 4 ml of Taq DNA polymerase to achieve the following end concentrations of formaldehyde: 0.2x stock solution (referred to as 0.2x); 0.18x stock solution; 0.16 x stock solution; 0.14x stock solution; 0.12x stock solution; 0.1x stock solution; 0.05 x stock solution; 0.03 x stock solution; 0.02 x stock solution; 0.01 x stock solution. The mixture was incubated for 30 min. at 37° C. in a temperature-controlled water bath, followed by quick chilling of the sample on ice and removing residual formaldehyde either by gel filtration or by ultrafiltration. To stabilize the formed complex, the modified enzyme was dialysed against a storage buffer containing 100 mM KCl; 0.1 mM EDTA; 0.5% (v/v) Tween 20; 0.5% (v/v) Nonidet P-40; 1 mM DTT; 10 mM ethanolamine; 50% glycerol; 20mM Tris/Cl; pH 9.0.

Example 4
Reduced Primer Extension Activity of Taq DNA Polymerase by Modification with Formaldehyde and Recovery of Primer Extension Activity After Heat-Treatment This example shows that primer extension activity of Taq DNA polymerase can be reduced by formaldehyde treatment and subsequently recovered by incubation at high temperature. The reduction of enzyme activity depends on the concentration of the formaldehyde and is not caused by the presence of formaldehyde itself in the primer extension reaction. The primer extension activity of the treated enzyme was recovered by heating at 90° C. for 30 min. The procedure describes an easy way to optimize the concentration and duration of formaldehyde treatment.

1 µl of Taq DNA polymerase (100 units) in above described storage buffer without detergents was treated with 10 µl in a final concentration of 0.3, 1 and 3 M of formaldehyde (Aldrich) for 10 min. at 37° C. then chilled on ice for 10 min. and diluted with 189 µl TE buffer (10 mM Tris HCl, pH 9.0 at 25° C., 1 mM EDTA). As a control, 1 µl of non-treated enzyme was mixed with 10 µl of formaldehyde solution to the final concentration of 0.3, 1 and 3 M of formaldehyde and immediately diluted (without heating) with 189 µl TE buffer to the required concentration.

Primer extension assays were performed as described in Example 1 with the following reaction profile: 94° C. for 1 sec., 55° C. for 30 sec., 72° C. for 12 min. The positive and negative controls correspond to the presence or absence of 0.5 units of Taq DNA polymerase diluted in the TE buffer without addition of additives.

In order to release the primer extension activity of Taq DNA polymerase, a reaction mixture of 40 µl containing 0.1 µM 30-mer oligonucleotide primer (SEQ ID NO:1), 50 µM of each dNTP in 10 µl of 10 mM Tris HCl pH 8.8 at 25° C., 50 mM KCl, 1.5 mM MgCl$_2$ and 4 µl of corresponding enzyme dilution was prepared. The reaction mixture was heated at 90° C. for 30 min. in a PTC-200 Thermocycler (MJ Research, Inc., Watertown, Mass.). 9 µl of the reaction mixture were mixed with 1 µl of 50 ng M13mp18 DNA. Primer extension reactions were performed with the following reaction profile: 94° C. for 1 sec., 55° C. for 30 sec., 72° C. for 12 min. The positive control consisted of 2 units Taq DNA polymerase diluted in TE buffer added to 40 µl of a starting mixture. As a negative control, the reaction mixture was thermocycled according to the above reaction profile, however no Taq DNA polymerase was added.

Example 5
Effect of Formaldehyde Concentration Used to Inactivate Taq DNA Polymerase on Primer Extension Activity This example describes the effect of formaldehyde concentration employed to inactivate Taq DNA polymerase on recovery of enzyme activity, as measured in a primer extension reaction as described in Example 1. Reaction mixtures containing either 0.01x, 0.02x, 0.03x, 0.05x, 0.1x, 0.18x Taq DNA polymerase were preincubated for 15 minutes at 95° C. Negative control contained no DNA polymerase. Assays were performed as described in Example 1, and the results below show relative primer extension activities of indicated Taq DNA polymerases normalized to 0.01× Taq DNA polymerase. Values indicate average activities determined from duplicate samples.

| Taq DNA polymerase | % primer extension activity |
|---|---|
| 0.01x | 100 |
| 0.02x | 78 |
| 0.03x | 64 |
| 0.05x | 62 |
| 0.1x | 62 |
| 0.18x | 59 |

The results demonstrate that recovery of enzyme activity is dependent on the formaldehyde concentration used to inactivate Taq DNA polymerase. However, 0.03× Taq DNA polymerase and Taq DNA polymerase preparations treated with higher formaldehyde concentrations showed no significant further decrease of primer extension activity.

Example 6
Effect of Pre-incubation Time

This example describes the effect of the pre-incubation time at 95° C. on recovery of enzyme activity, measured in a primer extension reaction as described in Example 1. Reaction mixtures containing 0.03× Taq DNA polymerase were preincubated for either 0, 7, 9, 12, 15 or 20 minutes at 95° C. A negative control mixture contained no Taq DNA polymerase. Recovery of primer extension activity was compared to a single-stranded M13 template completely converted into double-stranded DNA (control: 100%). Values indicate average activities determined from duplicate samples.

| Pre-incubation time at 95° C. | % primer extension activity |
|---|---|
| 0 min. | 0 |
| 7 min. | 9 |
| 9 min. | 18 |
| 12 min. | 27 |
| 15 min. | 40 |
| 20 min. | 71 |

The result demonstrates that Taq DNA polymerase treated with formaldehyde is completely inactive in a primer extension assay without previous heat incubation. Therefore, during PCR reaction setup at room temperature, no extension of misprimed oligonucleotides can occur. Furthermore, the result indicates that with increasing pre-incubation time at 95° C., recovery of enzyme activity increases. Enzyme activity becomes recovered by incubation at elevated temperature in a time-dependent manner.

Example 7
Nucleic Acid Amplification Reaction Using Inactivated Taq DNA Polymerases This example describes the use of inactivated Taq DNA polymerase for amplification of a nucleic acid template.
PCR Protocol PCR reactions were performed using either non-modified Taq DNA polymerase or 0.03× Taq DNA polymerase. 0.5 µl of each Taq DNA polymerase were used in each PCR reaction. A cloned HIV-I sequence was amplified with primers flanking a 497 bp PCR fragment from the HIV pol gene (including primer sequences, 24-mer 5'-ACAAGGGAAGGCCAGGGAATTTTC-3' (SEQ ID NO:2), 24-mer 5'-GGGCCATCCATTCCTGGCTTTAAT-3' (SEQ ID NO:3)). The reaction mixture contained 50 copies of the HIV genomic sequence and 10 mM Tris-HCl pH 8.7, 50 mM KCl, 1.5 mM MgCl$_2$, 200 µM of each dNTP, 0.5 µM of each primer, 1 µg human genomic DNA (purified from human whole blood using the QIAamp® Blood Kit, QIAGEN, Hilden, Germany) and 0.5 µl of either unmodified Taq DNA polymerase or 0.03× Taq DNA polymerase. Final reaction volume was 50 µl. The thermal cycling profile consisted of a pre-incubation step at 95° C. for 10 min., followed by 45 cycles: denaturation step for 1 min. at 94° C., and combined annealing/extension steps at 60° C. for 1 min. Amplification products were analyzed on a 1.5% agarose gel by gel electrophoresis using a 1× TAE electrophoresis buffer and a DNA intercalating dye. Gel electrophoresis was performed for approximately 35 min. at 85 volts. Ethidium bromide-stained amplification products were visualized using UV irradiation.

The results demonstrate that formaldehyde-modified Taq DNA polymerase useful for a hot-start PCR. Unmodified Taq DNA polymerase was not able to generate the expected PCR product, and additional stained bands observed on the control gel indicated non-specific amplification products. Specific amplification product was not detectable by gel electrophoresis when using unmodified Taq DNA polymerase in PCR. In contrast, 0.03× Taq DNA polymerase preparations generated the specific PCR product, and the amount of non-specific amplification products was markedly reduced when compared with the unmodified Taq DNA polymerase PCR products. This example demonstrates that Taq DNA polymerase, when inactivated with formaldehyde and reactivated by heat treatment, can significantly outperform non-modified Taq DNA polymerase with respect to specificity and sensitivity of PCR.

Example 8
Nucleic Acid Amplification Reaction Using Betaine and Inactivated Taq DNA Polymerase This example describes the beneficial use of PCR additives such as betaine in combination with inactivated Taq DNA polymerase for the amplification of difficult template sequences, such as, for example, reactions yielding non-specific PCR products, reactions involving templates with a high GC-content or extensive secondary structure.
PCR Protocol PCR reactions were performed using 0.03× Taq DNA polymerase. 0.25 µl of 0.03× Taq DNA polymerase was used in each reaction. A fragment of the human type-1 angiotensin II receptor gene was amplified with primers flanking a 321 bp PCR fragment (including primer sequences, 20-mer 5'-GCAACGCCCCTCACTATAAA-3' (SEQ ID NO: 6), 20-mer 5'-GCACCCCGCCCTTGAAGTCC-3' (SEQ ID NO: 7)). The reaction mixture contained 250 ng human genomic DNA purified from human whole blood using QIAamp® Blood Kit, (QIAGEN, Hilden, Germany), 20 mM Tris-HCL pH 8.4, 50 mM KCl, 1.5 mM MgCl$_2$, 200 µM of each dNTP, 0.5 µM of each primer and 0.25 µl of 0.03× Taq DNA polymerase. Reactions were performed in parallel without betaine and in the presence of 1M betaine (Sigma). Final reaction volume was 50 µl. The thermal cycling profile consisted of a pre-incubation step at 95° C. for 15 min., followed by 30 cycles: denaturation step for 1 min. at 94° C., annealing step for 1 min. at 50° C. and an extension step for 1 min. at 72° C. Amplification products were analyzed on a 1% agarose gel by gel electrophoresis using a 1× TAE electrophoresis buffer and a DNA intercalating dye. Gel electrophoresis was performed for approximately 35 min. at 85 volts. Ethidium bromide-stained amplification products were visualized using UV irradiation.

The results demonstrate that formaldehyde-inactivated Taq DNA polymerase can be used in combination with betaine to improve PCR reactions. Without betaine, inactivated Taq DNA polymerase was not able to generate the desired PCR product and produced instead faint non-specific amplification products. In contrast, in the presence of betaine, only the specific PCR product was amplified with high product yield. This example demonstrates that Taq DNA polymerase, when inactivated with formaldehyde and reactivated by heat treatment can be used in combination with PCR additives which affect the melting behavior of nucleic acids, preferably betaine, to enable PCR reactions or to improve specificity and sensitivity of PCR reactions.

Example 9
Effect of PCR Reaction Buffer System on Reactivation of Formaldehyde-Treated Taq DNA Polymerase Compared With Carboxylic Acid Anhydride-Treated Taq DNA Polymerase Unexpectedly, we found that formaldehyde-treated Taq DNA polymerase performed more reproducibly than carboxylic acid anhydride-inactivated Taq DNA polymerase (AmpliTaq® Gold, Perkin-Elmer, Norwalk, Conn.) when using PCR reaction buffer for Taq DNA polymerase provided by different Taq DNA polymerase suppliers. Therefore, in the present example, recovery of primer extension activity of either formaldehyde-treated 0.03× Taq DNA polymerase or carboxylic acid anhydride-treated Taq DNA polymerase (AmpliTaq® Gold, Perkin Elmer, Norwalk, Conn.) was compared in PCR reaction buffers supplied by Perkin Elmer (10×: 100 mM Tris-HCl pH 8.3 at 25° C., 500 mM KCl), Life Technologies (10×: 200 mM Tris-HCl pH 8.4 at 25° C., 500 mM KCl), Promega (10×: 100 mM Tris-HCl pH 9.0 at 25° C., 500 mM KCl, 1% Triton X-100) and Pharmacia (10×: 100 mM Tris-HCl pH 9.0 at room temperature, 500 mM KCl without Triton X-100). Equal unit activities of respective enzymes were employed in the assays. Assays were performed as described in Example 6, except that the pre-incubation time was 20 minutes at 95° C. Values represent the average of duplicate reactions.

|                     | % recovered primer extension activity | |
|---------------------|--------------------------|-----------------|
| PCR reaction buffer | 0.03× Taq DNA polymerase | AmpliTaq ® Gold |
| Perkin Elmer        | 74                       | 83              |
| Life Technologies   | 82                       | 69              |
| Promega             | 62                       | 14              |
| Pharmacia           | 44                       | 7               |

The results indicate that reactivation capability of formaldehyde-treated Taq DNA polymerase is more robust concerning different PCR reaction buffers than Taq DNA polymerase inactivated with carboxylic acid anhydride. Furthermore, with respect to the PCR buffer composition, it is apparent that the pH value of the reaction buffer dramatically influences the reactivation capability of carboxylic acid anhydride-treated Taq DNA polymerase.

Example 10
Effect of pH Value on Reactivation of Formaldehyde-Treated Taq DNA Polymerase Compared With Carboxylic Acid Anhydride-Treated Taq DNA Polymerase This example describes the capability of formaldehyde-treated 0.03× Taq DNA polymerase to recover enzyme activity by heat incubation in comparison with carboxylic acid anhydride-treated Taq DNA polymerase (AmpliTaq® Gold, Perkin Elmer, Norwalk, Conn.). Activity assays were performed as described in Example 8, except that a standard reaction buffer was used containing 100 mM Tris-HCl pH 8.3–9.0 at 20° C. and 500 mM KCl without detergents. Pre-incubation was carried out for 20 minutes at 95° C. Values represent the average of duplicate reactions.

|                     | % recovered primer extension activity | |
|---------------------|--------------------------|-----------------|
| Reaction buffer pH  | 0.03× Taq DNA polymerase | AmpliTaq ® Gold |
| 8.3                 | 50                       | 53              |
| 8.4                 | 56                       | 37              |
| 8.5                 | 44                       | 16              |
| 8.6                 | 47                       | 16              |
| 8.7                 | 61                       | 0               |
| 8.8                 | 47                       | 0               |
| 8.9                 | 38                       | 0               |
| 9.0                 | 20                       | 0               |

The results demonstrate that recovery of enzyme activity of formaldehyde-treated Taq DNA polymerase is independent of reaction buffer pH. In contrast, Taq DNA polymerase that has been inactivated using carboxylic acid anhydride showed significant decrease of primer extension activity with increasing pH of the reaction buffer. At pH values above 8.6, no activity of this Taq DNA polymerase was measured.

The pH of the reaction buffer or reaction mixture is of great importance for optimal enzyme activity. Different enzymes possess different individual optimal pH values at which they exhibit the best performance. Even among functionally similar enzymes such as thermostable DNA polymerases, optimal pH value of the reaction buffer varies from pH 7.5 (Bca DNA polymerase, Uemori et al., *J. Biochem.* (*Japan*), 113(3):401–10 (1993)) to pH 10 (Tfl DNA polymerase, Kaledin et al., *Biokhimiia* (*USSR*) 46(9): 1576–84 (1981)). Additionally, even distinct enzymatic activities present in the same enzyme may possess different pH optima. For example 3'-5' exonuclease activity contained in so-called proofreading DNA polymerases usually require a high pH value of above pH 8.8 for optimal proofreading activity, which is required for high fidelity PCR reactions.

To compare the effects and basic capabilities of formaldehyde and carboxylic acid anhydride on inactivation and recovery of enzyme activity in thermostable enzymes in general, one such proofreading enzyme, Pfu DNA polymerase (from *Pyrococcus furiosus*) was used as a model system. Furthermore, Pfu DNA polymerase belongs to a completely different DNA polymerase family that is isolated from archeabacteria, representing a completely different kingdom of organisms than *Thermus aquaticus*, which belongs to eubacteria.

Pfu DNA polymerase was treated with either of two inhibitors, formaldehyde and citraconic anhydride.

Example 11
Preparation of Inactivated Pfu DNA Polymerase Using Formaldehyde

This example shows the modification of Pfu DNA polymerase with formaldehyde.

Pfu DNA polymerase was modified in exactly the same way as described for Taq DNA polymerase in Example 3, with the exception that the enzyme was used at concentrations of 2–5 U/µl.

Example 12
Preparation of Inactivated Pfu DNA Polymerase and Taq DNA Polymerase Using Citraconic Anhydride Pfu DNA polymerase and Taq DNA polymerase were prepared according to the method described in European patent publication EP 0 771 870 A1, which is hereby incorporated by reference. Preparations contained a molar ratio 240x of citraconic anhydride to each of the thermostable DNA polymerases (Taq and Pfu).

Example 13
Influence of pH on PCR Performance of Formaldehyde- and Citraconic Anhydride-Inactivated Pfu DNA Polymerase and Taq DNA Polymerase This example shows a comparison of either 0.03x Taq DNA polymerase and 240x Taq DNA polymerase or 0.03x Pfu DNA polymerase and 240x Pfu DNA polymerase in PCR. In contrast to Taq DNA polymerase, the pH optimum for PCR of Pfu DNA polymerase was reported to be pH 8.8. PCR reactions were carried out in a PCR reaction buffer for Taq DNA polymerase: 10 mM Tris-HCl pH 8.3 or pH 8.7, 50 mM KCl; or in a reaction buffer for Pfu DNA polymerase: 20 mM Tris-HCl pH 8.3 or pH 8.8; 10 mM KCl; 10 mM $(NH_4)_2SO_4$; 2 mM $MgSO_4$; 0.1% Triton X-114.

PCR Protocol

PCR reactions were performed using either unmodified Taq DNA polymerase, formaldehyde-treated 0.03x Taq DNA polymerase, 240x citraconic anhydride-treated Taq DNA polymerase, or AmpliTaq® Gold (Perkin Elmer, Norwalk, Conn.); or either unmodified Pfu DNA polymerase, formaldehyde-treated 0.03x Pfu DNA polymerase, or 240x citraconic anhydride-treated Pfu DNA polymerase. 0.5 μl of each DNA polymerase preparation were used in each PCR reaction. A portion of a plasmid construct derived from vector pUC19 containing the complete $lacI^q$ sequence was amplified with primers: 24-mer, 5'-CTTCGCCCACCCCGGGCTCGATCC-3' (SEQ ID NO: 4) and 25-mer, 5'-CATGAAGCACTTCACTGACACCCTC-3' (SEQ ID NO:5). The reaction mixture contained 5 ng plasmid DNA (purified with QIAGEN tip 100, QIAGEN, Hilden, Germany), 200 μM of each dNTP, 0.2 μM of each primer, respective reaction buffers and 0.5 μl of indicated thermostable DNA polymerase. Enzyme activity was recovered by heat incubation at 95° C. for either 0, 5 or 15 minutes. The thermal cycling profile consisted of said pre-incubation step, followed by 45 cycles, denaturation step for 30 seconds at 94° C., annealing step at 60° C. for 1 min. and extension at 72° C. Amplification products were analyzed on a 1.5% agarose gel by electrophoresis using a 1x TAE electrophoresis buffer and a DNA intercalating dye. Gel electrophoresis was performed for approximately 35 min. at 85 volts. Ethidium bromide-stained amplification products were visualized using UV irradiation.

Results

All Taq DNA polymerase preparations produced the expected PCR product, with similar PCR product yield, when the PCR reaction buffer was pH 8.3. Furthermore, PCR product yield increased with increasing pre-incubation time at 95° C. In contrast, only 0.03x Taq DNA polymerase (formaldehyde-treated) yielded the same result when using the same PCR buffer at pH 8.7. No amplification products were obtained with either AmpliTaq® Gold or 240x citraconic anhydride-treated Taq DNA polymerase. PCR reactions using Pfu DNA polymerase are commonly performed using a PCR buffer of pH 8.8 for optimal PCR conditions. Accordingly, none of the Pfu DNA polymerase preparations including non-inactivated Pfu DNA polymerase were able to synthesize a PCR product in Pfu PCR reaction buffer of pH 8.3. When using Pfu PCR reaction buffer of pH 8.8, the expected PCR product could be obtained with non-inactivated Pfu DNA polymerase. Also 0.03x Pfu DNA polymerase inactivated with formaldehyde produced the PCR product with similar yield. In contrast, citraconic anhydride-treated Pfu DNA polymerase did not generate any PCR products demonstrating that formaldehyde inactivation is much more applicable than anhydride-mediated inactivation for Pfu DNA polymerase.

Example 14
Effect of Nucleic Acid Sample Preparation on PCR Performance of Formaldehyde- and Citraconic Anhydride-Inactivated Taq DNA Polymerase Nucleic acid samples often vary with purity, contaminating substances, and pH. In the case of purifying nucleic acids with commercially available kits like the QIAamp® Blood Kit (QIAGEN, Hilden, Germany), the pH of the nucleic acid sample is often adjusted to high pH values, e.g., pH 9.0. In order to investigate the influence of such nucleic acid samples on amplification reactions, PCR reactions performed with either formaldehyde treated 0.03x Taq DNA polymerase or AmpliTaq® Gold (Perkin Elmer, Norwalk, Conn.) were spiked with nucleic acid samples of varying pH. Amplification reactions were carried out in a final volume of 50 μl spiked with 25 μl of nucleic acid sample. The pH of DNA samples was either 8.0, 8.5 or 9.0. Controls were performed with addition of the appropriate volume of PCR grade water (QIAGEN, Hilden Germany).

The target sequence was a 497 bp DNA sequence (including primer sequences) of the HIV-I polymerase gene cloned into a plasmid using reaction conditions and primers as described in Example 7. PCR reactions contained 50 copies of the HIV-I containing plasmid DNA and 250 ng human genomic DNA in 25 μl spiked into the PCR assays.

Results

In the presence of formaldehyde-treated Taq DNA polymerase, yields of the amplified PCR product from reactions spiked with 25 μl nucleic acid sample remained comparable with that of the amplification control. In contrast, when using AmpliTaq® Gold (Perkin Elmer, Norwalk, Conn.), PCR product yield decreased with increasing pH of the spiked nucleic acid sample, demonstrating that the nature of the nucleic acid sample can negatively influence the performance of the PCR reaction, dependent on the method used to inactivate the thermostable DNA polymerase. Again, this example indicates that the inactivation of thermostable enzymes using an aldehyde such as formaldehyde is more suitable for molecular biology applications compared with the method using dicarboxylic acid anhydrides.

Example 15
Continuous Reverse Transcription Polymerase Chain Reaction (RT-PCR) using a Combination of Reverse Transcriptase and Inactivated Taq DNA Polymerase This example describes the use of inactivated Taq DNA polymerase in combination with a reverse transcriptase for a continuous reverse transcription polymerase chain reaction (RT-PCR) in a single reaction tube without interrupting the enzymatic reactions by additional handling steps.

RT-PCR protocol

Coupled reverse transcriptase and PCR reactions were performed in single tubes using 0.03x Taq DNA polymerase and either avian myeloblastosis virus reverse transcriptase (AMV, Boehringer Mannheim) or a RNase H negative form of the Moloney murine leukaemia virus reverse transcriptase (SUPERSCRIPT™ II, Life Technologies) 0.5 µl of 0.03× Taq DNA polymerase was used in each reaction as well as either 5 units AMV or 100 units SUPERSCRIPT™ II. A fragment of the human glycerinaldehyde-3-phosphate-dehydrogenase gene was reverse transcribed from total RNA into complementary DNA (cDNA) by either reverse transcriptase and subsequently amplified by 0.03× Taq DNA polymerase using primers flanking a 831 bp PCR fragment including primer sequences (24-mer 5'-ATGGGGAAGGTGAAGGTCGGAGTC-3' (SEQ ID NO: 8), 24-mer 5'-AGTGTAGCCCAGGATGCCCTTGAG-3' (SEQ ID NO: 9)) for both enzymatic reactions. The reaction mixture contained 1 µg total RNA from HeLa cells (purified from human HeLa cell line using RNeasy® Maxi Kit, QIAGEN, Hilden, Germany), 20 mM Tris-HCl pH 8.4, 50 mM KCl, 1.5 mM MgCl$_2$, 200 µM of each dNTP, 0.4 µM of each primer. Final reaction volume was 50 µl. The thermal cycling profile consisted of a 30 min. lasting reverse transcriptase step at 50° C., directly followed by a pre-incubation step at 95° C. for 15 min. during which simultaneously the respective reverse transcriptase became inactivated. This step was followed by 40 cycles: denaturation step for 30 sec. at 94° C., annealing step for 45 sec. at 55° C. and an extension step for 1 min. at 72° C. Amplification products were analyzed on a 1% agarose gel by gel electrophoresis using a 1× TAE electrophoresis buffer and a DNA intercalating dye. Gel electrophoresis was performed for approximately 35 min. at 85 volts. Ethidium bromide-stained amplification products were visualized using UV irradiation.

The results demonstrate that formaldehyde-inactivated Taq DNA polymerase can be used in combination with reverse transcriptases in a continuous single tube RT-PCR reaction. Advantageously, formaldehyde-inactivated Taq DNA polymerase is inactive during the reverse transcriptase reaction and only becomes active for the PCR reaction, while during the heat activation step, residual reverse transcriptase activity is destroyed. This advantageous effect of formaldehyde-inactivated Taq DNA polymerase can be used in continuous single tube RT-PCR with both RNase H positive and RNase H negative reverse transcriptases.

Additional embodiments of the present invention will be apparent to those skilled in this art from the foregoing disclosure. All such additional embodiments are within the scope of the invention as defined in the claims to follow.

What is claimed is:

1. A modified thermostable DNA polymerase, produced by a reaction, under essentially aqueous conditions, of a thermostable DNA polymerase and a modifier reagent at a temperature of less than 50° C., wherein said modifier reagent is an aldehyde of the formula RHC=O, where R is H or an alkyl, aryl, or alkylaldehyde group of 1 to 10 carbon atoms, and wherein said reaction results in a thermally reversible inactivation of the DNA polymerase.

2. The modified thermostable DNA polymerase according to claim 1, wherein incubation of said modified thermostable enzyme at a temperature of at least 50° C. results in at least a two-fold increase in enzyme activity.

3. The modified thermostable DNA polymerase according to claim 1, wherein the modification has been carried out in the presence of 0.01 M to 2 M modifier reagent.

4. The modified thermostable DNA polymerase according to claim 1, wherein said reagent is an aldehyde selected from water soluble aldehydes capable of forming crosslinks between amino-functional side chains of enzyme amino acids.

5. The modified thermostable DNA polymerase of claim 1, wherein said reagent is formaldehyde.

6. The modified thermostable DNA polymerase according to claim 1, wherein said polymerase is derived from an organism selected from the genera Thermus, Pyrrococcus or Thermotoga.

7. The modified thermostable DNA polymerase according to claim 1, wherein said polymerase is derived from an organism selected from the group consisting of *Thermus aquaticus, Thermus thermophilus, Thermus flavus, Pyrococcus furiosus, Pyrococcus woesei,* Pyrococcus spec. (strain KOD1), Pyrococcus spec. GB-D, *Thermococcus litoralis,* Thermococcus sp. 9° N-7, *Thermotoga maritima,* Pyrococcus spec. ES4 (*endeavori*), Pyrococcus spec. OT3 (*horikoshii*),*Pyrococcus profundus, Thermococcus stetteri,* thermococcus spec. AN1 (*zilligii*), *Thermococcus peptonophilus, Thermococus celer,* and *Thermococcus fumicolans.*

8. The modified thermostable DNA polymerase according to claim 1, wherein said polymerase is derived from an organism selected from the group consisting of *Thermus aquaticus, Pyrococcus furiosus,* and *Pyrococcus woesei.*

9. A polymerase chain reaction amplification reaction mixture comprising: (a) a modified thermostable DNA polymerase according to claim 1; and (b) a set of polymerase chain reaction specific primers.

10. A mixture according to claim 9, further including a PCR additive affecting the melting behavior of a nucleic acid.

11. A mixture according to claim 10, wherein said PCR additive is selected from the group consisting of betaines, multifunctional polyols, amides, alkaline ammonia salts, sulfoxides, sulfates, SSB proteins, and calf thymus protein UP1.

12. A mixture according to claim 11, wherein said PCR additive is selected from the group consisting of betaines, glycerol, formamide, tetramethylammonium chloride, dimethylsulfoxide, polyethylene glycol, *E. coli* SSB protein, T4 gene 32 protein, yeast SSB protein, and calf thymus protein UP1.

13. A mixture according to claim 11, wherein said PCR additive is betaine.

14. A reagent kit for performing polymerase chain reaction comprising a modified thermostable DNA polymerase according to claim 1.

15. A reagent kit according to claim 14, further including a PCR additive affecting the melting behavior of a nucleic acid.

16. A reagent kit according to claim 15, wherein said PCR additive is selected from the group consisting of betaines, multifunctional polyols, amides, alkaline ammonia salts, sulfoxides, sulfates, SSB proteins, and calf thymus protein UP1.

17. A reagent kit according to claim 16, wherein said PCR additive is selected from the group consisting of betaines, glycerol, formamide, tetramethylammonium chloride, dimethylsulfoxide, polyethylene glycol, *E. coli* SSB protein, T4 gene 32 protein, yeast SSB protein, and calf thymus protein UP1.

18. A reagent kit according to claim 16, wherein said PCR additive is betaine.

19. A reagent mixture for performing polymerase chain reaction comprising a modified thermostable DNA polymerase according to claim 1.

20. A reagent mixture according to claim 19, further including a PCR additive affecting the melting behavior of a nucleic acid.

21. A reagent mixture according to claim 20, wherein said PCR additive is selected from the group consisting of betaines, multifunctional polyols, amides, alkaline ammonia salts, sulfoxides, sulfates, SSB proteins, and calf thymus protein UP1.

22. A reagent mixture according to claim 21, wherein said PCR additive is selected from the group consisting of betaines, glycerol, formamide, tetramethylammonium chloride, dimethylsulfoxide, polyethylene glycol, *E. coli* SSB protein, T4 gene 32 protein, yeast SSB protein, and calf thymus protein UP1.

23. A reagent mixture according to claim 21, wherein said PCR additive is betaine.

24. A method for the amplification of a target nucleic acid comprising the step of:

(a) contacting said nucleic acid with an amplification reaction mixture containing a modified thermostable enzyme, wherein said modified thermostable enzyme is produced by a reaction, under essentially aqueous conditions, of a thermostable enzyme and a modifier reagent at a temperature of less than 50° C., wherein said modifier reagent is an aldehyde of the formula RHC=O, where R is H or an alkyl, aryl, or alkylaldehyde group of 1 to 10 carbon atoms, and wherein said reaction results in thermally reversible inactivation of the enzyme.

25. The method of claim 24, wherein said modifier reagent is formaldehyde.

26. The method according to claim 25, wherein said thermostable enzyme is a polymerase.

27. The method according to claim 25, wherein said thermostable enzyme is a DNA polymerase.

28. The method according to claim 27, wherein said polymerase is derived from an organism selected from the genera Thermus, Pyrrococcus or Thermotoga.

29. The method of claim 27, wherein said polymerase is derived from an organism selected from the group consisting of *Thermus aquaticus, Thermus thermophilus, Thermus flavus, Pyrococcus furiosus, Pyrococcus woesei,* Pyrococcus spec. (strain KOD1), Pyrococcus spec. GB-D, *Thermococcus litoralis,* Thermococcus sp. 9° N-7, *Thermotoga maritima,* Pyrococcus spec. ES4 (*endeavori*), Pyrococcus spec. OT3 (*horikoshii*), *Pyrococcus profundus, Thermococcus stetteri,* Thermococcus spec. AN1 (*zilligii*), *Thermococcus peptonophilus, Thermococcus celer,* and *Thermococcus fumicolans.*

30. The method of claim 24, wherein said modified thermostable enzyme is prepared by a reaction of a thermostable polymerase in the presence of 0.01 M to 2 M modifier reagent at a temperature of less than 50° C.

31. The method of claim 24, wherein said thermostable enzyme is a polymerase derived from *Thermus aquaticus* and said modifier reagent is formaldehyde.

32. The method of claim 24, wherein said reaction mixture further comprises a PCR additive affecting the melting behavior of said nucleic acid.

33. The method of claim 32, wherein said PCR additive is selected from the group consisting of betaines, multifunctional polyols, amides, alkaline ammonia salts, sulfoxides, sulfates, SSB proteins, and calf thymus protein UP1.

34. The method of claim 33, wherein said PCR additive is selected from the group consisting of betaines, glycerol, formamide, tetramethylammonium chloride, dimethylsulfoxide, polyethylene glycol, *E. coli* SSB protein, T4 gene 32 protein, yeast SSB protein, and calf thymus protein UP1.

35. The method of claim 33, wherein said PCR additive is betaine.

36. A polymerase chain reaction amplification mixture comprising:

(a) a modified thermostable enzyme according to claim 1;

(b) a set of polymerase chain reaction specific primers;

(c) a reverse transcriptase; and (d) a nucleic acid.

37. The reaction mixture of claim 36 wherein said nucleic acid is ribonucleic acid.

38. The reaction mixture of claim 36 wherein said reverse transcriptase is RNase H positive or RNase H negative.

39. The polymerase chain reaction amplification mixture of claim 36 further comprising a PCR additive affecting the melting behavior of the nucleic acids.

40. The reaction mixture of claim 39 wherein said PCR additive is betaine.

* * * * *